US005700485A

United States Patent [19]
Berde et al.

[11] Patent Number: 5,700,485
[45] Date of Patent: Dec. 23, 1997

[54] PROLONGED NERVE BLOCKADE BY THE COMBINATION OF LOCAL ANESTHETIC AND GLUCOCORTICOID

[75] Inventors: Charles B. Berde, Brookline; Robert S. Langer, Newton, both of Mass.

[73] Assignee: Children's Medical Center Corporation, Boston, Mass.

[21] Appl. No.: 432,402

[22] Filed: May 1, 1995

Related U.S. Application Data

[63] Continuation-in-part of Ser. No. 119,958, Sep. 10, 1993, which is a continuation-in-part of Ser. No. 943,287, Sep. 10, 1992, abandoned.

[51] Int. Cl.[6] .................................................. A61K 9/16
[52] U.S. Cl. ........................ 424/501; 424/499; 424/426; 514/818
[58] Field of Search ............... 424/486, 499, 424/501, 426, 428; 514/818, 951, 952

[56] References Cited

U.S. PATENT DOCUMENTS

| | | | |
|---|---|---|---|
| 3,185,625 | 5/1965 | Brown | 167/82 |
| 3,755,558 | 8/1973 | Scribner | 424/47 |
| 3,972,995 | 8/1976 | Tsuk et al. | 424/28 |
| 4,034,758 | 7/1977 | Theeuwes | 128/260 |
| 4,039,653 | 8/1977 | DeFoney et al. | 424/19 |
| 4,059,686 | 11/1977 | Tanaka et al. | 424/19 |

(List continued on next page.)

FOREIGN PATENT DOCUMENTS

| | | | |
|---|---|---|---|
| 0 195 906 | 2/1986 | European Pat. Off. | A61K 31/71 |
| 0 244 118 | 4/1987 | European Pat. Off. | A61K 9/10 |
| WO 91/17772 | 11/1991 | WIPO | A61K 47/30 |
| WO 92/07555 | 5/1992 | WIPO | A61K 9/22 |
| WO 93/20138 | 10/1993 | WIPO | |
| WO 95/09613 | 4/1995 | WIPO | |

OTHER PUBLICATIONS

Leong K. et al., Bioerodable Polyanhydride as Drug–carrier Matrices. I: Characterization, Degradation, and Release Characteristics, *Journal of Biomedical Materials Research* 19:941–955 (1985).
Conix A. Poly [1,3–bis(p–carboxyphenoxy) propane anhydride], *Macro. Snyth.* 2:95–98 (1966).

(List continued on next page.)

*Primary Examiner*—Edward J. Webman
*Attorney, Agent, or Firm*—Arnall Golden & Gregory, LLP

[57] ABSTRACT

Biodegradable controlled release microspheres for the prolonged administration of a local anesthetic agent, and a method for the manufacture thereof are disclosed. The microspheres are formed of a biodegradable polymer degrading significantly within a month, with at least 50% of the polymer degrading into non-toxic residues which are removed by the body within a two week period. Useful polymers include polyanhydrides, polylactic acid-glycolic acid copolymers and polyorthoesters containing a catalyst; polylactic acid-glycolic acid copolymers are preferred. Local anesthetics are incorporated into the polymer using a method that yields a uniform dispersion, preferably solvent casting. Prolonged release is obtained by incorporation of a glucocorticoid into the polymeric matrix or by co-administration of the glucocorticoid with the microspheres. The type of anesthetic and the quantity are selected based on the known pharmaceutical properties of these compounds.

21 Claims, 7 Drawing Sheets

U.S. PATENT DOCUMENTS

| | | | |
|---|---|---|---|
| 4,070,347 | 1/1978 | Schmitt | 260/77.5 |
| 4,093,709 | 6/1978 | Choi et al. | 424/19 |
| 4,131,648 | 12/1978 | Choi et al. | 424/22 |
| 4,138,344 | 2/1979 | Choi et al. | 252/1 |
| 4,226,848 | 10/1980 | Nagai et al. | 424/19 |
| 4,250,163 | 2/1981 | Nagai et al. | 424/14 |
| 4,369,172 | 1/1983 | Schor et al. | 424/19 |
| 4,434,153 | 2/1984 | Urquhart et al. | 424/22 |
| 4,530,840 | 7/1985 | Tice et al. | 514/179 |
| 4,542,025 | 9/1985 | Tice et al. | 424/78 |
| 4,568,535 | 2/1986 | Loesche | 424/19 |
| 4,568,536 | 2/1986 | Kronenthal et al. | 424/22 |
| 4,569,837 | 2/1986 | Suzuki et al. | 424/28 |
| 4,585,651 | 4/1986 | Beck et al. | 424/88 |
| 4,591,496 | 5/1986 | Cohen et al. | 424/15 |
| 4,597,960 | 7/1986 | Cohen | 424/28 |
| 4,622,244 | 11/1986 | Lapka et al. | 427/213.32 |
| 4,638,045 | 1/1987 | Kohn et al. | 530/323 |
| 4,650,665 | 3/1987 | Kronenthal et al. | 424/435 |
| 4,652,441 | 3/1987 | Okada et al. | 424/19 |
| 4,685,883 | 8/1987 | Jernberg | 433/215 |
| 4,713,244 | 12/1987 | Bawa et al. | 424/429 |
| 4,732,155 | 3/1988 | Zetter et al. | 128/630 |
| 4,735,945 | 4/1988 | Sakamoto et al. | 514/279 |
| 4,753,652 | 6/1988 | Langer et al. | 623/1 |
| 4,757,128 | 7/1988 | Domb et al. | 528/271 |
| 4,779,806 | 10/1988 | Langer et al. | 241/1 |
| 4,780,320 | 10/1988 | Baker | 424/493 |
| 4,789,724 | 12/1988 | Domb et al. | 528/176 |
| 4,806,621 | 2/1989 | Kohn et al. | 528/211 |
| 4,857,311 | 8/1989 | Domb et al. | 424/78 |
| 4,861,627 | 8/1989 | Mathiowitz et al. | 427/213.31 |
| 4,863,735 | 9/1989 | Kohn et al. | 424/422 |
| 4,886,870 | 12/1989 | D'Amore et al. | 528/206 |
| 4,891,225 | 1/1990 | Langer et al. | 424/428 |
| 4,898,734 | 2/1990 | Mathiowitz et al. | 424/426 |
| 4,900,556 | 2/1990 | Wheatley et al. | 424/450 |
| 4,906,474 | 3/1990 | Langer et al. | 424/428 |
| 4,916,204 | 4/1990 | Domb et al. | 528/271 |
| 4,919,939 | 4/1990 | Baker | 424/493 |
| 4,921,737 | 5/1990 | Wheatley et al. | 428/402.2 |
| 4,933,185 | 6/1990 | Wheatley et al. | 424/461 |
| 4,933,431 | 6/1990 | Domb et al. | 528/328 |
| 4,946,929 | 8/1990 | D'Amore et al. | 528/206 |
| 5,075,109 | 12/1991 | Tice et al. | 424/88 |
| 5,122,367 | 6/1992 | Ron et al. | 242/80 |
| 5,188,837 | 2/1993 | Domb | 424/450 |
| 5,227,165 | 7/1993 | Domb et al. | 424/450 |

OTHER PUBLICATIONS

Brown L. et al., Controlled Release of Insulin from Polymer Matrices: Control of Diabetes in Rats, *Diabetes* 35:692–697 (1987).

Brem H. et al., Interstiatial Chemotherapy with rug Polymer Implants for the Treatment of Recurrent Gliomas, *Journal of Neurosurgery* 74:441–446 (1986).

Brem H. et al., Biocompatibility of a Biodegradable Controlled–release Polymer in the Rabbit Brain. *Sel Cancer Ther* 5(2):55–65 (1989).

Sharon C. et al., *Development of Drug Delivery Systems for Use in Treatment of Narcotic Addiction, Naltrexone: Research Monograph 28*, Edited by Willette RE, Barnette G. Nat. Institute on Drug Abuse, 194–213 (1980).

Langer R., New Methods of Drug Delivery, *Science*, 228:190 (1985).

Bonica, John J. and F. Peter Buckley, "Regional Analgesia with Local Anesthetics," *The Management of Pain* II:1883–1966 (1990), Lea & Febiger (Eds.) Second Edition.

Devor, Marshall, et al., "Corticosteroids Suppress Ectopic Neural Discharge Originating in Experimental Neuromas," *Pain* 22:127–137 (1985).

McCleane, G., et al., "The addition of triamcinoione acetonide to bupivacaine has no effect on the quality of analgesia produced by ilioinguinal nerve block," *Anaesthesia* 4:819–820 (1994).

Anderson, J.M., et al., "The role of the fibrous capsule in the function of implanted drug–polymer sustained released systems," *J. Biomed. Mater. Res.*, 15, 889–902 (1981).

Berde, C.B., et al., Abstracts of Scientific Papers, 1990 Annual Meeting, Amer. Soc. Anesthesiologists, 73:A776 (Sep. 1990).

Christenson, L., et al., "Mast cells and tissue reaction to intraperitoneally implanted polymer capsules," *J. Biomed. Mater. Res.*, 25, 1119–1131 (1991).

Christenson, L., et al., "Tissue reaction to intraperitoneal polymer implants: Species difference and effects of corticoid and doxorubicin," *J. Biomed. Mater. Res.*, 23, 705–718 (1989).

Haynes, Duncan H., et al., "Ultra–long–duration Local Anesthesia Produced by Injection of Lecithin–coated Methoxyflurane Microdroplets," *Anesthesiology* 63:490–499 (1985).

Iannotti, J.P., et al., "Synthesis and Characterization of Magnetically Responsive Albumin Microspheres Containing cis–Hydroxyproline for Scar Inhibition," *Orthop. Res. Soc.*, 9, 432–444 (1991).

Ingher, Donald and Judah Folkman, "Inhibition of Angiogenesis Through Modulation of Collagen Metabolism," *Lab. Invest.*, 59, 44–51 (1988).

Ksander, George A., et al., "Experimental effects on surrounding fibrous capsule formation from placing steroid in a silicone baggel prosthesis before implantation," *Plast. & Reconstr. Surg.*, 62, 873–883 (1978).

Lewis, D.H., et al., "The Use of In Vitro Release Methods to Guide the Development of Controlled–Release Formulations," 9th International Symposium on Controlled Release of Bioactive Materials, Sponsored by Controlled Release Society, Inc.

Martyn, J.A.J., et al., "Up–and–down Regulation of Skeletal Muscle Acetylcholine Receptors," *Anesthesiology* 76:822–843 (1992).

Masters, D.B., et al., Meeting of the American Society of Anesthesiologists 75:A680 (1991).

Masters, David B., et al., "High Sensitivity Quantification of RNA from Gels and Autoradiograms with Affordable Optical Scanning," *BioTechniques* 12:902–911 (1992).

Masters, D.B., et al., "Prolonged Sciatic Nerve Blockage Using Sustained Release of Veratridine from a Biodegradable Polymer Matrix," *Soc. Neurosci. Abstr.* 18:200 (1992).

Schneider, Markus, et al., "A Preferential Inhibition of Impulses in C–fibers of the Rabbit Vagus Nerve by Veratridine an Activator of Sodium Channels," *Anesthesiology* 74:270–281 (1991).

Terranova, Victor, P., et al., "Biochemically mediated periodontal regeneration," 248.

Tice, Thomas R., et al., "Controlled Release of Ampicillin and Gentamicin From Biodegradable Microcapsules," 108–111.

Tice, T.R., et al., "Development of Microencapsulated Antibiotics for Topical Administration," 168–170.

Too, Heng–Phon and John E. Maggio, "Radioimmunoassay of Tachykinins," *Methods in Neurosciences*, edited by Conn PM, New York, Academic Press, 1991, pp. 232–247.

Wakiyama, Naoki et al., "Preparation and Evaluation in Vitro and in Vivo og Polylactic Acid Microspheres containing Dibucaine," *Chem. Pharm. Bull.* 30:3719–3727 (1982).

Wakiyama, Naoki et al., "Influence of Physicochemical Properties of Polylactic Acid on the Characteristics and in Vitro Release Patterns of Polyactic Acid Microspheres containing Local Anesthetics," *Chem. Pharm. Bull.* 30:2621–2626 (1982).

Principles of Membrane Diffusion, 22–38.

"Avenues for the Medical Control of Abnormal Neural Discharge," *Textbook of Pain Wall and Melzack* (Churchill Livingstone 1994).

Devor, et al., "Corticosteoids Suppress Ectopic Neural Discharge Originating in Experimental Neuromas," *Pain* 22, 127–137 (1985).

Duncan, et al., "Treatment of Upper Extremity Reflex Sympathetic Dystrophy with Joint Stiffness Using Sympatholytic Bier Blocks and Manipulation" *Orthopedics* 11(6), 883–886 (1988).

Flanagan, et al., "Intra–articular injection for pain relief in patients awaiting hip replacement," *Ann. Royal Coll. Surg. Eng.* 70, 156–157 (1988).

Glasser, et al., "The perioperative use of corticosteroids and bupivacaine in the management of lumbar disc disease," *J. Neurosurg.* 78, 383–387 (1993).

Guttu, et al., "Delayed Healing of Muscle After Injection of Bupivicaine and Steroid" *Annals of Dentistry* 49:5–8 (1990).

Hall, et al., "Acute effects of intravenous glucorticoid on cat spinal motor neuron electrical properties," *Brain Research* 240, 186–190 (1982).

Johansson, et al., "Local corticosteroid application blocks transmission in normal nociceptive C–fibres," *Acta Anaesthesiol. Scand.* 34, 335–338 (1990).

Sandrock and Warfield, "Epidural Steroids and Facet Injections," Ch. 29 *Principles and Practice of Pain Management* Warfield, C.A., editor (McGraw–Hill, Inc. 1993).

Waldman, et al.,"The Relief of Body Wall Pain Secondary to Malignant Hepatic Metastases by Intercostal Nerve Block with Bupivicaine and Methylprednisolone," *J. Pain Symptom Management* 3(1), 39–43 (1988) (see in particular p. 42, col. 2).

Williams, D.L., et al., "Microencapsulated Local Anesthetics," Proc. Int. Symp. Rel. Bioact. Mater. 11:69–70 (1984).

PROLONGED NERVE BLOCKADE BY THE COMBINATION OF LOCAL ANESTHETIC AND GLUCOCORTICOID

This is a continuation-in-part of U.S. Ser. No. 08/119,958 filed Sep. 10, 1993, which is a continuation-in-part of U.S. Ser. No. 07/943,287, filed Sep. 10, 1992 by Charles B. Berde and Robert S. Langer, now abandoned.

The U.S. Government has rights in this invention pursuant to National institutes of Health Grant No. GM-15904 to Harvard Anesthesia Research and Teaching Center to C. Berde, and Grant No. CA 5257 to R. Langer.

BACKGROUND OF THE INVENTION

This invention is generally in the field of anesthesiology and, in particular, the delivery of anesthetic agents which locally block pain for periods of time of between a few hours and days, up to weeks.

In order to provide local or regional blockade for extended periods, clinicians currently use local anesthetics administered through a catheter or syringe to a site where the pain is to be blocked. This requires repeated administration where the pain is to be blocked over a period of greater than one day, either as a bolus or through an indwelling catheter connected to an infusion pump. These methods have the disadvantage of potentially causing irreversible damage to nerves or surrounding tissues due to fluctuations in concentration and high levels of anesthetic. In addition, anesthetic administered by these methods are generally neither confined to the target area, nor delivered in a linear, continuous manner. In all cases, analgesia rarely lasts for longer than six to twelve hours, more typically four to six hours. In the case of a pump, the infusion lines are difficult to position and secure, the patient has limited, encumbered mobility and, when the patient is a small child or mentally impaired, may accidentally disengage the pump.

Drugs are typically administered in a variety of ways, including by injection, topical administration, oral ingestion, and sustained release devices. Methods which provide for systemic, rather than localized, delivery are not an option with local anesthetics since these could interfere with the patient's ability to breathe, if administered systemically. Devices could potentially provide for a sustained, controlled, constant localized release for longer periods of time than can be achieved by injection or topical administration. These devices typically consist of a polymeric matrix or liposome from which drug is released by diffusion and/or degradation of the matrix. The release pattern is usually principally determined by the matrix material, as well as by the percent loading, method of manufacture, type of drug being administered and type of device, for example, microsphere. A major advantage of a biodegradable controlled release system over others is that it does not require the surgical removal of the drug depleted device, which is slowly degraded and absorbed by the patient's body, and ultimately cleared along with other soluble metabolic waste products.

Systemic anesthetics such as methoxyflurane, have been incorporated into liposomes and lecithin microdroplets, for example, as described by Haynes, et al., *Anesthesiology* 63:490–499 (1985). To date, the liposome and lecithin preparations have not been widely applied in clinical or laboratory practice, because of their inability to provide dense blockade for a prolonged period of time (i.e., three or more days) in a safe and controlled manner. The lecithin microdroplets and liposomes degrade or are phagocytized too rapidly, in a matter of hours. Other lipid based devices, formed in combination with polymer, for release of local anesthetics are described by U.S. Pat. No. 5,188,837 to Domb.

Local anesthetics have been incorporated into biodegradable polymeric devices, for example, polylactic acid microspheres, as described by Wakiyama, et al., *Chem. Pharm. Bull.*, 30:3719–3727 (1982). In contrast to the lipid based materials, the poly(lactic acid) devices take over a year to degrade and cause localized inflammation. Berde, et al., Abstracts of Scientific Papers, 1990 Annual Meeting, Amer. Soc. Anesthesiologists, 73:A776 (September 1990), reported the use of a device formed of a polyanhydride polymer matrix of copolymer 1,3 bis (p-carboxyphenoxy) propane and sebacic acid, in a ratio of 1:4, into which dibucaine free base was incorporated by compression molding. This drug-polymer device, however, had several drawbacks. For example, because the drug was incorporated into the polymer matrix by compression molding, the device sometimes displayed bulk erosion, causing fast initial release of drug. In addition, the device often generated an inflammatory response or a capsule of serous material or fibrin, which is particularly a problem when located adjacent to nerves.

Other studies have reported encapsulation of local anesthetics such as bupivacaine or tetracaine in polyanhydride or poly-lactic-glycolic acid polymeric microspheres, Masters (1993), Masters (1993), and Lim (1995). Sensory and motor blockade in these studies lasted for periods of one to ten days, depending on the type of preparation and dose used. While implantable, the microspheres were not small enough to inject.

Accordingly, it is the object of this invention to provide an improved biodegradable controlled release device which administers local anesthetic for a prolonged period of time which is injectable.

It is a further object of the present invention to provide a method and means for modulating the rate of release of the local anesthetic from the bioerodible polymer matrix through variations in microsphere composition and size.

SUMMARY OF THE INVENTION

Biodegradable controlled release microspheres for the prolonged administration of a local anesthetic agent, and a method for the manufacture thereof are disclosed. The microspheres are formed of a biodegradable polymer degrading significantly within a month, with at least 50% of the polymer degrading into non-toxic residues which are removed by the body within a two week period. Useful polymers include polyanhydrides, polylactic acid-glycolic acid copolymers and polyorthoesters containing a catalyst; polylactic acid-glycolic acid copolymers are preferred. Local anesthetics are incorporated into the polymer using a method that yields a uniform dispersion, preferably solvent casting. Prolonged release is obtained by incorporation of a glucocorticoid into the polymeric matrix or by co-administration of the glucocorticoid with the microspheres. The type of anesthetic and the quantity are selected based on the known pharmaceutical properties of these compounds.

The microspheres are injected at the site where the anesthetic is to be released. This can be at the time of surgery, or following removal of systemic anesthetic.

Examples demonstrate prolongation of release of the combination as compared with release in the absence of the glucocorticoid. Other types of steroids and antiinflammatories did not extend release, nor was prolonged release shown in vitro.

DETAILED DESCRIPTION OF THE INVENTION

Figure 1A:
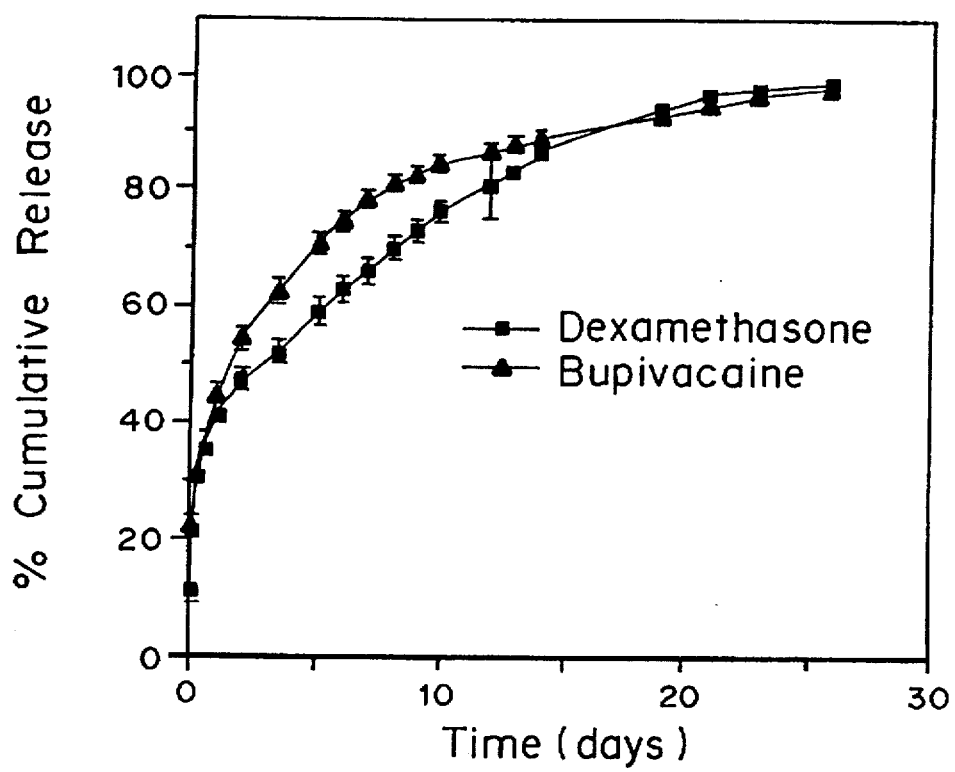
FIG. 1a is a graph of percent cumulative release versus time (days) for release from microspheres formed of polylactic acid-glycolic acid (PLGA), 75:25, with (squares) and without (triangles) 0.05% dexamethasone.

Microsphere systems for the controlled and prolonged delivery of a local anesthetic agent to a targeted area are provided. These systems can be used for the management of various forms of persistent pain, such as postoperative pain, sympathetically maintained pain, or certain forms of chronic pain such as the pain associated with many types of cancer.

Polymers

It is important that the polymer degrade in vivo over a period of less than a year, with at least 50% of the polymer degrading within six months or less. More preferably, the polymer will degrade significantly within a month, with at least 50% of the polymer degrading into non-toxic residues which are removed by the body, and 100% of the drug being released within a two week period. Polymers should also degrade by hydrolysis by surface erosion, rather than by bulk erosion, so that release is not only sustained but also linear. Polymers which meet this criteria include some of the polyanhydrides, copolymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1% by weight anhydride catalyst such as maleic anhydride. Other polymers include protein polymers such as gelatin and fibrin and polysaccharides such as hyaluronic acid. Polylactic acid is not useful since it takes at least one year to degrade in vivo.

The polymers should be biocompatible. Biocompatibility is enhanced by recrystallization of either the monomers forming the polymer and/or the polymer using standard techniques.

Anesthetics

The systems employ biodegradable polymer matrices which provide controlled release of local anesthetics. As used herein, the term "local anesthetic" means a drug which provides local numbness or pain relief. A number of different local anesthetics can be used, including dibucaine, bupivacaine, etidocaine, tetracaine, lidocaine, and xylocaine. The preferred anesthetic is bupivacaine or dibucaine, most preferably in the form of a salt, for example, the hydrochloride, bromide, acetate, citrate, or sulfate. Compared to the free base form of these drugs, the more hydrophilic hydrochloride salt displays longer and denser nerve block, more complete release from polymer matrices, slower clearance from the targeted nerve area, and less encapsulation. Bupivacaine is a particularly long acting and potent local anesthetic when incorporated into a PLAM. Its other advantages include sufficient sensory anesthesia without significant motor blockage, lower toxicity, and wide availability.

The devices can also be used to administer local anesthetics that produce modality-specific blockade, as reported by Schneider, et al., Anesthesiology, 74:270–281 (1991), or that possess physical-chemical attributes that make them more useful for sustained release then for single injection blockade, as reported by Masters, et al., Soc. Neurosci. Abstr., 18:200 (1992), the teachings of which are incorporated herein.

The anesthetic is incorporated into the polymer in a percent loading of 0.1% to 90% by weight, preferably 5% to 75% by weight. It is possible to tailor a system to deliver a specified loading and subsequent maintenance dose by manipulating the percent drug incorporated in the polymer and the shape of the matrix, in addition to the form of local anesthetic (free base versus salt) and the method of production. The amount of drug released per day increases proportionately with the percentage of drug incorporated into the matrix (for example, from 5 to 10 to 20%). In the preferred embodiment, polymer matrices with about 75% drug incorporated are utilized, although it is possible to incorporate substantially more drug, depending on the drug, the method used for making and loading the device, and the polymer.

Antiinflammatories

Glucocorticoids that are useful to prolong in vivo release include glucocorticocoids such as dexamethasone, cortisone, prednisone, and others routinely administered orally or by injection. Useful loadings are from 0.01 to 30% by weight, preferably between 0.05 and 0.5%. The dosage must be low enough to avoid toxicity.

The examples demonstrate that glucocortocoids such as dexamethasone prolong release in vivo and not in vitro, but do not reduce the intensity of the nerve block generated by the release of anesthetic from the polymer, and do not affect the recovery of sensation and strength. Other compounds do not prolong release.

Methods of Manufacture

The microspheres are preferably manufactured using a method that evenly disperses the anesthetic throughout the device, such as solvent casting, spray drying or hot melt, rather than a method such as compression molding. Microparticles, microspheres, and microcapsules are collectively referred to herein as "microspheres". A desired release profile can be achieved by using a mixture of microspheres formed of polymers having different release rates, for example, polymers releasing in one day, three days, and one week, so that linear release is achieved even when each polymer per se does not release linearly over the same time period.

Methods for manufacture of microspheres are well known and are typified in the following examples. In the preferred embodiment for administration by injection, the microspheres have a diameter of between approximately 10 and 200 microns, more preferably between 20 and 120 microns.

Methods of Administration

In the preferred method of administration, the microspheres are administered by injection at the site where pain relief is to be achieved. The microspheres may be injected through a trochar, or the pellets or slabs may be surgically placed adjacent to nerves.

As described below, the microspheres can be administered alone or in combination with a solution including a steroidal anti-inflammatory or other glucocorticoids in an amount effective to prolong release of anesthetic from the microspheres. Alternatively, the microspheres include an amount of steroidal anti-inflammatory effective to prolong release of anesthetic from the microspheres.

Potential applications include two to five day intercostal blockade for thoracotomy, or longer term intercostal blockade for thoracic post-therapeutic neuralgia, lumbar sympathetic blockade for reflex sympathetic dystrophy, or three-day ilioinguinal/iliohypogastric blockade for hernia repair.

The present invention is further described with reference to the following non-limiting examples.

The following methods were utilized in the in vivo studies on rats,

Nerve Block Tests

Motor Block

The rats were behaviorally tested for sensory and motor blockage in a quiet observation room at 24±1° C. Testing was only performed in rats showing appropriate baseline hot plate latencies after at least one week of testing. In all testing conditions, the experimenter recording the behavior was unaware of the side containing the local anesthetic. To assess motor block, a 4-point scale based on visual observation was devised: (1) normal appearance, (2) intact dorsiflexion of foot with an impaired ability to splay toes when elevated by the tail, (3) toes and foot remained plantar flexed with no splaying ability, and (4) loss of dorsiflexion, flexion of toes, and impairment of gait. For graphing clarity, partial motor block equals a score of 2 and dense motor block is a score of either 3 or 4.

Sensory Block

Sensory blockade was measured by the time required for each rat to withdraw its hind paw from a 56° C. plate (IITC Life Science Instruments, Model 35-D, Woodland Hills, Calif.). They were tested between 10 am and 12 pm daily and allowed to adjust to their surroundings in a quiet room at 22±1° C. for at least 30 minutes before testing. The rats were held with a cloth gently wrapped above their waist to restrain the upper extremities and obstruct vision. The rats were positioned to stand with one hind paw on a hot plate and the other on a room temperature plate. With a computer data collection system (Apple IIe with a footpad switch), latency to withdraw each hind paw to the hot plate was recorded by alternating paws and allowing at least fifteen seconds of recovery between each measurement. If no withdrawal occurred from the hot plate within 15 seconds, the trial was terminated to prevent injury and the termination time was recorded. Testing ended after five measurements per side, the high and low points were disregarded, and the mean of the remaining three points was calculated for each side. Animals were handled in accordance with institutional, state and federal guidelines.

No rats were observed to have inflammation or blisters. Rats were tested for at least two weeks prior to surgery to achieve a consistent baseline latency, and testing continued for two weeks after surgery to confirm complete recovery from sensory blockade. Motor blockade was rated on a 4-point scale. Animals with a motor block of 4 had a clubbed hindpaw and usually dragged their affected leg when walking. Motor block 3 animals walked normally but had toes that failed to splay when the animal was lifted. Animals with motor block of 2 showed toes that splayed but not as fully as normal or motor block 1 animals.

Necropsy and Histology

Animals were sacrificed two weeks after implantation. Sections of sciatic nerve approximately 2–3 cm in length, adjacent and proximal to the implants, were preserved in 10% formalin solution (24 mM sodium phosphate, pH 7). Sections were then embedded in paraffin, stained with hematoxylin and eosin, and examined by light microscopy.

Plasma Analysis

Rats (250–275 g) anesthetized with ketamine-HCl (100 mg/ml at 1.5 ml/kg, i.p.) and xylazine (4 mg/ml at 4 mg/kg, i.p.), were implanted with a silastic catheter into the right jugular vein. Blood was withdrawn (0.5 cc) before implantation and at timed intervals after administration via the indwelling central venous cannulae. Plasma was extracted with an equal volume of HPLC grade methanol (Fischer Scientific, Pittsburgh, Pa.), centrifuged (10,000×g) and the methanol phase filtered (0.2 μm nylon syringe type, Rainin, Woburn, Mass.) prior to HPLC analysis. The HPLC reliably quantified bupivacaine concentrations in the plasma methanol extraction phase down to 10 ng/ml. The bupivacaine standards used for blood plasma analyses were added to plasma aliquots prior to methanol extraction. The peak matching the standard bupivacaine peak's retention time was verified in plasma samples by doping with bupivacaine.

Statistics

Data were analyzed using linear regression tests, ANOVA, Chi Square tests and Wilcoxon rank-sum tests, where appropriate.

EXAMPLE 1

In Vivo and In Vitro Release Profile of PLAMs Containing Anesthetic in Combination with Antiinflammatory As described in U.S. Ser. No. 08/199,958 filed Sep. 10, 1993, depending upon the method of preparation, it was common in the previous studies to observe some encapsulation around the PLAM at autopsy two weeks following implantation. Encapsulation involves formation of a fibrous material around foreign bodies. It begins with attempts by granulocytes to phagocytose and incorporate the foreign material during the initial acute inflammatory response. The process of encapsulation through fibrosis is due to histiocytes and fibroblasts, which generate the layers of collagenous connective tissue surrounding the implant. Encapsulation depends upon several factors, including the chemical and physical characteristics of the implant, the mechanical action of the implant, its site in the body and the presence of microorganisms.

The effects of dexamethasone and cis-hydroxyproline on inflammation, encapsulation and duration of sensory and motor blockade following implantation of bupivacaine-impregnated polymer matrices along the sciatic nerves of rats were therefore determined. Each drug had been shown separately in other studies to act upon different components of the inflammatory process. (L. Christenson, L. Wahlberg, and P. Aebischer, "Mast cells and tissue reaction to intraperitoneally implanted polymer capsules," *J. Biomed. Mater. Res.*, 25, 1119–1131 (1991); L. Christenson, P. Aebischer, P. McMillian, and P. M. Galletti, "Tissue reaction to intraperitoneal polymer implants: species difference and effects of corticoid and doxorubicin," *J. Biomed. Mater. Res.*, 23, 705–718 (1989); D. Ingber and J. Folkman, "Inhibition of angiogenesis through modulation of collagen metabolism," *Lab. Invest.*, 59, 44–51 (1988); and J. P. Iannotti, T. C. Baradet, M. Tobin, A. Alavi, and M. Staum, "Synthesis and characterization of magnetically responsive albumin microspheres containing cis-hydroxyproline for scar inhibition," *Orthop. Res. Soc.*, 9, 432–444 (1991)). Their individual effects on reducing encapsulation and improving drug release behavior were examined in this study.

Methods and Materials

Implants

Copolymers of 1,3-bis(p-carboxyphenoxy)propane and sebacic acid (20:80) were synthesized and recrystallized to remove impurities. PLAMs containing 10% and 20% L-cis-hydroxyproline (CHP) by weight of CPP:SA (20:80) copolymer or containing 20% crystalline bupivacaine-HCL by weight of CPP:SA 20:80 copolymer were produced using the hot melt procedure. PLAMs incorporating both bupivacaine and dexamethasone (dexamethasone) were synthesized via the hot melt procedure, using a uniform mixture of dexamethasone and bupivacaine formed by combining dexamethasone dissolved in 95% ethanol with bupivacaine dissolved in 95% ethanol. The solution was air-dried under the hood at room temperature until the ethanol evaporated and left behind a well-dispersed mixture of dry crystalline dexamethasone and bupivacaine. The crystalline mixture was pulverized under mortar and pestle and combined with copolymer. Control PLAMs contained only CPP:SA (20:80) copolymer and all pellets were synthesized with large bore Teflon® tubing.

Two different dosage sets of dexamethasone/bupivacaine PLAMs were produced: high dose (hd) dexamethasone and low dose (ld) dexamethasone. Hd-dexamethasone/bupivacaine PLAMs contained approximately 60 µg dexamethasone per pellet. Ld-dexamethasone/bupivacaine PLAMs contained approximately 15 µg per pellet. Both sets contained 20% bupivacaine by weight.

In Vitro Studies

Tritium labeled dexamethasone ($^3$H-dexamethasone) was purchased from New England Nuclear Corporation (Boston, Mass.). An aliquot consisting of $10^7$ counts was added to a mixture of 200 µg unlabelled dexamethasone and 190 mg bupivacaine dissolved in 95% ethanol. This solution was air-dried under the hood at room temperature until the ethanol evaporated and left behind a well-dispersed mixture of dry crystalline $^3$H-labelled dexamethasone, unlabelled dexamethasone and bupivacaine. This dry crystalline mixture was pulverized under mortar and pestle and combined with 650 mg CPP:SA (20:80) copolymer. All $^3$H-dexamethasone/unlabelled dexamethasone/bupivacaine PLAMs were synthesized using large bore Teflon® tubing. Each pellet was placed in 5 mL of sterile 1× PBS (phosphate-buffered saline) containing 1% sodium azide and incubated at 37° C. The incubated 1× PBS media was removed and stored at –20° C., and replaced with 5 ml of fresh sterile 1× PBS at 2 h, 6 h and 24 h time points and then once daily thereafter for 3 weeks. The $^3$H released was counted using a liquid scintillation counter (Rackbeta 1214).

In Vivo Studies

Animals were implanted with 3 hd-dexamethasone/bupivacaine PLAM pellets on the experimental side. Animals were implanted with 3 ld-dexamethasone/bupivacaine PLAM pellets on the experimental side. Control animals were implanted with 3 control PLAM pellets on the control side.

Surgery

All animals were anesthetized with 3.5%–4.0% halothane in oxygen and maintained with 1.5%–2.0% halothane. Anesthesia was achieved within 3–5 minutes post induction. Animals were tested by pinching of tailbase and pawpads to confirm the anesthetic state. The thigh area was shaved and an incision was made directly below the greater trochanter. The hamstrings were gently divided by blunt dissection to expose the sciatic nerve. PLAM pellets were placed adjacent to the sciatic nerve under direct vision in the fascial plane deep to the hamstrings and the site was irrigated with 0.5 cc of antibiotic solution (5000 units/mL penicillin G sodium and 5000 ug/mL streptomycin sulfate) to prevent infection. The most superficial facial layer was closed with a single suture. The edges of the outer skin were approximated and closed with one to two surgical staples.

For all rats, drug-containing PLAMS were implanted on the experimental side. The control (contralateral) side varied among the groups.

Necropsy

For autopsy, the skin of the dorsal thigh was removed. A midline transverse cut was made through each successive layer of hamstring muscle to locate the site of encapsulation, if any, and preserve its integrity and architecture. The capsule was excised by blunt dissection and placed in 10% formalin. A 3 cm segment of the sciatic nerve was removed from its exit point at the greater sciatic foramen to its branching point above the dorsal aspect of the knee joint. For light microscopy, a segment was fixed in 10% buffered formalin.

Histology

Nerves: For evaluation of sciatic nerves, cross-sections were processed, embedded in paraffin and sectioned at 2 μm and stained with hematoxylin eosin. 5-10 sections were studied via light microscopy by a pathologist in a blinded manner. Each cross-section was evaluated for (1) epineural inflammation, (2) epineural fibrosis, and (3) subperineural fibroblasts. Each parameter was rated on a severity scale of 0-4. A score of 0=no change, 1=mild, 2=moderate, 3=moderate-severe and 4=severe.

Capsules: Encapsulation was evaluated by gross examination at the time of dissection and through photographs by a blinded observer. This evaluation was divided into 3 categories. The first type was characterized by no true capsule. It involved nonspecific, unorganized inflammatory debris surrounding the implantation site. The other two capsule types were classified according to the manner of Ksander, et al. (G. A. Ksander, L. M. Vistnes and D. C. Fogerty, "Experimental effects on surrounding fibrous capsule formation from placing steroid in a silicone bag-gel prosthesis before implantation," *Plast. & Reconstr. Surg.*, 62, 873–883 (1978)). The second type was characterized by flimsiness, an ability to be easily deformed and torn, and an irregular dull surface of white to gray color. This type was designated as a diffuse capsule. The third type was characterized by toughness, resistance to deformation by handling and tearing at excision, and a smooth glossy inner surface of yellowish-brown to clear translucence. This type was designated as a laminar capsule. It was a true histological capsule with highly organized, fibrous walls enclosing the implanted pellets, completely separating it from immediate surrounding tissue. A severity scale of 0-4, similar to that described above, was used to rank the degree of inflammation of the perineural fascia and muscle fascia.

Cross-sections of formalin-fixed capsules were examined by light microscopy and rated on a severity scale from 0-4, specifically looking at (1) thickness of capsule wall, (2) proportion of PMN's in relation to other inflammatory cells, (3) proportion of lymphocytes to other inflammatory cells, (4) proportion of plasma cells to other inflammatory cells, (5) proportion of foreign body giant cells to other inflammatory cells, (6) proportion of immature fibroblasts to mature fibroblasts, and (7) extent of collagen deposition in the capsule wall.

RESULTS

In Vitro Release of Dexamethasone

The release of dexamethasone from PLAM was nearly linear for the first 8 days and eventually reached a plateau by Day 21. Approximately 60% of dexamethasone was released from PLAM by Days 7-8 and by Day 21, 97% of dexamethasone was released.

In Vivo Results

The protocols and results are shown in Table 1.

TABLE 1

| | | Classification of Capsules | | | |
|---|---|---|---|---|---|
| Group # | Type of Side | PLAM Type | No capsule | Diffuse capsule | Laminar capsule |
| 1 | experimental | 10% CHP + bup | | | 4 |
| 3b | experimental | bupivacaine | | | 4 |
| 4 | experimental | bupivacaine | | | 6 |
| 4 | control | control | | | 6 |
| 5 | control | control | | 1 | 4 |
| 7 | control | control | | 3 | 2 |
| 5 | experimental | ld-dexamethaso ne/bup | 5 | | |
| 6 | experimental | hd-dexamethaso ne/bup | 5 | | |
| 7 | experimental | hd-dexamethaso ne | 5 | | |

Histology

Dexamethasone prevented capsule formation in all groups whose experimental side received dexamethasone-containing PLAM pellets. In contrast, CHP did not prevent encapsulation. All groups treated with CHP formed capsules around implants by the time of dissection. Groups implanted with bupivacaine PLAMs and no additive (dexamethasone or CHP) developed capsules around implants. Groups which received lo control PLAMs also formed capsules around implants. dexamethasone-treated sides were significantly different from contralateral control sides implanted with drug-free PLAMs ($p<0.0001$). They were also statistically different from sides receiving CHP-($p=0.0003$) and/or bupivacaine-containing PLAM pellets ($p<0.0001$). Capsules formed from drug-free PLAMs (control PLAMs) were histologically indistinguishable from those that resulted from drug-containing PLAMs (CHP and bupivacaine).

Nerves

All groups showed no statistical significance between experimental and control sides in all three inflammatory factors examined: (1) epineural inflammation, (2) epineural fibrosis, and (3) perineural fibroblasts.

Sensory and Motor Blockade Among Animals Treated with Dexamethasone and CHP

Animals implanted with ld-dexamethasone/bupivacaine PLAMs had the longest sensory and motor blockade. Sensory blockage lasted for a period of 6-7 days with maximum block intensity (latency=12 sec) observed on days 1-5 in all animals. Motor blockade lasted for 6-8 days with the densest motor block seen on day 1-5. All animals returned to baseline on Day 8. Rats implanted with hd-dexamethasone/bupivacaine PLAMs also had sensory block lasting 6-7 days. However, maximum block intensity was observed only on days 1-2 in all rats. A plateau of dense block (latency=7-11 sec) was seen on days 3-5. Motor blockade lasted for 3-5 days with the densest motor block occurring on day 1-2. Group 4 animals (control group receiving large bore bupivacaine PLAMs) had sensory blockade lasting 5-6 days. There were no time points when all animals had maximum block intensity simultaneously. However, dense sensory block (latency=7-11 sec) was observed on days 1-4 in all animals. Motor blockade lasted 3-6 days with densest block seen on Days 1-2. Rats, who were implanted with hd-dexamethasone PLAMs, showed no sensory and motor block, and all time points could not be distinguished from baseline. Rats who were implanted with 10% CHP PLAM plus bupivacaine PLAMs, 20% CHP PLAMs and plus bupivacaine PLAMs, and bupivacaine PLAMs alone, respectively, all displayed similar sensory block durations and intensities. All groups showed sensory block durations of 2–4 days with dense block seen on Day 1 and the majority of rats returning to baseline on Days 2–4. Duration of motor block lasted for 1–2 days with the densest block observed primarily on day 1.

Plasma Assays for ACTH and Corticosterone

Plasma assays showed no difference in ACTH and corticosterone levels compared to normal values of rats taken at the same period of day and under similar stress-level conditions.

EXAMPLE 2

Prolonged Nerve Blockade with Steroidal Antiinflammatories

Since the implantable devices require surgery to use, it is more desirable to make microspheres (Ms) which can be injected. However, in order to obtain sensory or motor blockade for greater than one day, it was necessary to add dexamethasone (D) to microspheres. Addition of 0.05% D prolonged block by five to ten fold.

Methods and Material

Abbreviations include PLGA, poly-lactic-glycolic acid; $CH_2Cl_2$, methylene chloride; PLAM, polymer local anesthetic matrices; dpm, disintegrations per minute; cpm, counts per minute; rpm, revolutions per minute.

The non-radioactive polymer microspheres used in this study were supplied by Medisorb, Cincinnati, Ohio. The 65/35 PLGA (Lot. No. S2170 Si177, Mw 130,000) was supplied by Medisorb, Cincinnati, Ohio. Tritium labeled dexamethasone was obtained from Amersham (specific activity $9.24 \times 10^{10}$ dpm/µmole) Bupivacaine free base was supplied by Purdue Frederick (Lot No. 32931) and dexamethasone was supplied by Sigma (Lot No. 34H0502). Trisma base was supplied by Sigma (Lot No. 64H5732). Dulbecco's phosphate-buffered saline was supplied by Gibco, Maryland. (Lot No. 14N5447). (KCL 2.68 mM\L, $KH_2PO_4$ 1.47 mM\L, NaCl 547.5 mM\L, $NaHPO_4$ 9.50 mM\L). The suspension media used in the in vivo experiments was supplied by Medisorb and consisted of 0.5% wv sodium carboxymethylcellulose (medium viscosity) and 0.1% wv Tween 80. A Coulter® Multisizer II, Coulter Electronics Ltd., Luton, England was used to determine the mass median diameter of the microspheres.

Polymer synthesis and Local Anesthetic Incorporation

The radiolabeled microspheres were formulated by a single emulsion technique, using an evaporation process. Two types of radiolabeled microspheres were formulated, one which contained 75% w/w unlabeled bupivacaine and 0.05% w/w tritium labeled dexamethasone and the other contained 0.05% w/w unlabeled dexamethasone and 75% w/w tritium labeled bupivacaine. The microspheres which contained tritium labeled dexamethasone were prepared as follows: an aliquot of dexamethasone containing $8 \times 10^6$ disintegrations per minute (dpm) was added to 100 µls of a solution of 5 mg of unlabeled dexamethasone in 5 mls of ethanol. The sample was dried under a stream of nitrogen for one hour and 50 mg of PLGA 65:35 and 150 mg of bupivacaine free base in 1 ml of $CH_2CL_2$ were added. The tube was vortexed for 1 minute at 2000 rpm on a Fisher Scientific Touch Mixer, Model 232. The 1 ml of 0.3% polyvinylalcohol in 100 mM Trisma® (tris(hydroxymethyl) amino methane) base (pH adjusted to 8.4) was added, and an emulsion formed by vortexing for 45 seconds. The emulsion was then poured into 100 mls of 0.1% polyvinylacohol in 100 mM Trisma® base. The $CH_2CL_2$ was removed from the microspheres using a rotary evaporator under vacuum at 40° C. for 20 minutes. After 2–3 minutes bubbles formed indicated that the organic solvent was being removed. The microspheres were sieved through a series of stainless steel sieves of pore sizes 140µ, 60µ and 20µ (Neward Wire Co.). Those microspheres which were less than 20 and greater than 140 microns in diameter were discarded. The microspheres which fell in the size range 20µ to 140µ were centrifuged at 4000 rpm for 5 minutes rinsed with buffer and centrifuged again. The microspheres were than frozen in liquid nitrogen and lyophilized overnight. The microspheres were examined before and after solven removal using an American Opitcal One–Ten light microscope to ensure that no leaching of the drug took place. If leaching did occur, the bupivacaine crystallized and could be seen even at 10× using a light microscope.

The microspheres which contained tritium labeled bupivacaine were formulated as described above with the following exceptions: An aliquot of radiolabeled bupivacaine consisting of $9 \times 10^6$ dpm was added to 150 mg of unlabeled bupivacaine free base. The solution was then vortexed to ensure homogeneous mixing of labeled and unlabeled bupivacaine. The ethanol was then removed under a stream of nitrogen for 1 hour. Upon removal of the ethanol, 50 mg of 65/35 PLGA and 100 µl from a solution dexamethasone 1 mg/ml in ethanol was added. Thereafter, the protocol was the same as that used to formulate microspheres which contained radiolabeled dexamethasone.

In order to determine the drug content, 5 mg of microspheres were dissolved in 2 mls of $CH_2Cl_2$ and the local anesthetic concentration determined by U.V. spectroscopy. The absorbance at 272 nm was read and compared to a calibration curve of known amounts (0 to 2.5 mg/ml) of bupivacaine free base dissolved in $CH_2Cl_2$.

In Vitro Release Studies

Unlabeled Microspheres 5 mg of microspheres were weighed out and 2 mls of Dulbecco's phosphate-buffered saline was added. The pH of the buffer was adjusted to 7.4 and 0.1% sodium azide was added as an antimicrobial agent. The buffer was changed at 0.5, 2, 6, 12, and 24 hours and once daily thereafter. The amount of bupivacaine free base in the buffer was determined using a Hewlett Packard 8452 Diode Array Spectrophotometer at 272 nm. Duplicates fron each batch of microspheres were assayed. Release media incubated with control microspheres which did not contain bupivacaine showed insignificant absorbance at 272 nm.

Labeled Microspheres

The procedure used to determine the in vitro release of both bupivacaine and dexamethasone is the same as that used for non-radiolabeled microspheres, except that the amount of radiolabeled compound released into the buffer was determined by adding 17 mls of Ecolume® scintillation fluid to 2 mls of buffer. The total number of counts was determined using a LKB Wallac 1214 Rackbeta Liquid Scintillation Counter. The efficiency, (the counts per minute/ disintegration per minute), of the counter was determined to be 51%. Five replications of each set of radiolabeled microspheres were used.

Preparation of Microsphere Suspensions for Injection and In Vivo Testing

The dose used varied between 50 and 450 mg of drug/kg of rat, and 0.6 mls of injection vehicle was used for each injection. The injection vehicle consisted of 0.5% w/w sodium carboxy methyl cellulose and 0.1% w/w Tween 80 in water. The microspheres in the suspending media were vortexed at maxium speed for two minutes prior to injection. The injection was performed by locating and injecting slightly below and proximal to the greater trochanter. Rats were anesthetized with halothane 2-3% inspired concentration in oxygen during injections, at least five rats were used to test each formulation.

Testing for Sciatic Nerve Block

Male Sprague-Dawley Charles River rats weighing between 200 and 350 mg were used to determine the duration of the block obtained with each of the different microsphere formulations tested. They were handled daily and habituated to the testing paradigm prior to exposure to local anesthetic injections. Sensory and motor blockade were examined as described above. The duration of the sensory block was determined as the length of time for which the latency was greater than or equal to 7 seconds.

In addition to sensory testing, motor testing was performed at each time point to examine the rat's ability to hop and to place weight on its hind leg. Animals were handled and cared for according to institutional, state, and federal regulation, and according to the guidelines of the International Associationi for the Study of Pain, Seattle, Wash.

RESULTS

Microsphere Morphology

Using the preparative procedures outlined above, smooth, spherical, mechanically stable microspheres were produced without significant quantities of crystalline bupivacaine leaching out the microspheres. When the drug leached out of the microspheres into the aqueous solution, it was in the form of long crystals, approximately 30μ in length and was visble by light microscopy. Comparison of PLGA microspheres loaded with 75% bupivacaine and 0.05% dexamethasone formulated by solvent removal using a vaccum at 40° C. with those formulated by stirring the microspheres at room temperature and pressure, for three hours until the organic solvent evaporated, showed no differences. Increasing the rate of removal of the organic solvent using heat and vaccum reduced the rate of leaching of bupivacaine out of the microspheres from 40% to 2%.

In vitro Release Kinetics

Figure 2:
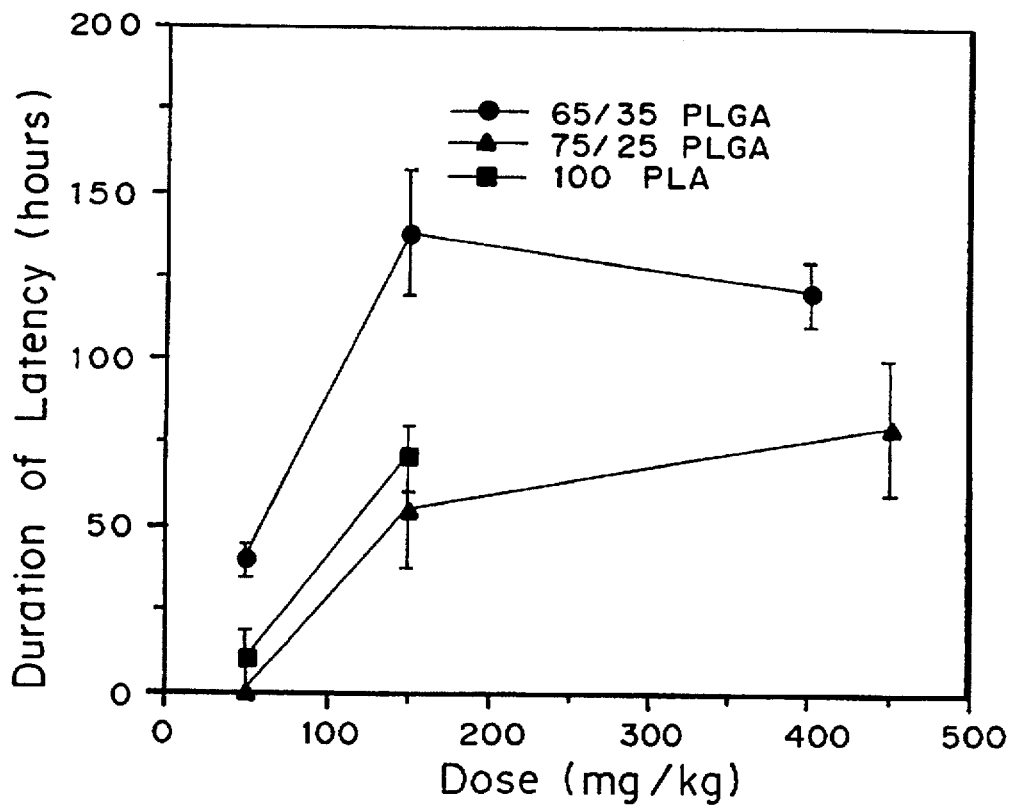
FIG. 2 is a graph of the dose response curve (duration of latency, hr) for polylactic acid (PLA) (squares), PLGA 65:35 (circles), and PLGA 75:25 microspheres loaded with bupivacaine and dexamethasone, administered at doses of 50 mg of microspheres/kg rat. Error bars indicate standard errors.

FIG. 1a compares the rates of in vitro release of bupivacaine from PLGA 75/25 microspheres loaded with 75% bupivacaine containing dexamethasone with those which did not contain dexamethasone. Bupivacaine is released at similar rates in both cases, so the presence of dexamethasone did not influence the rate of diffusion of bupivacaine out of the polymer microspheres. The similar in vitro release rates of bupivacaine from PLGA 50/50, 65/35, 75/25 PLGA and PLA are shown in FIG. 2. Comparison of the % cumulative release of bupivacaine from microspheres when the pH of the buffer media was 6, 7.4 and 8 shows that the rate of release of bupivacaine was higher at pH 6 than at pH 7.4 or 8, because bupivacaine has greater water solubility at pH 6 than at pH 7.4 or pH 8.

Figure 1B:
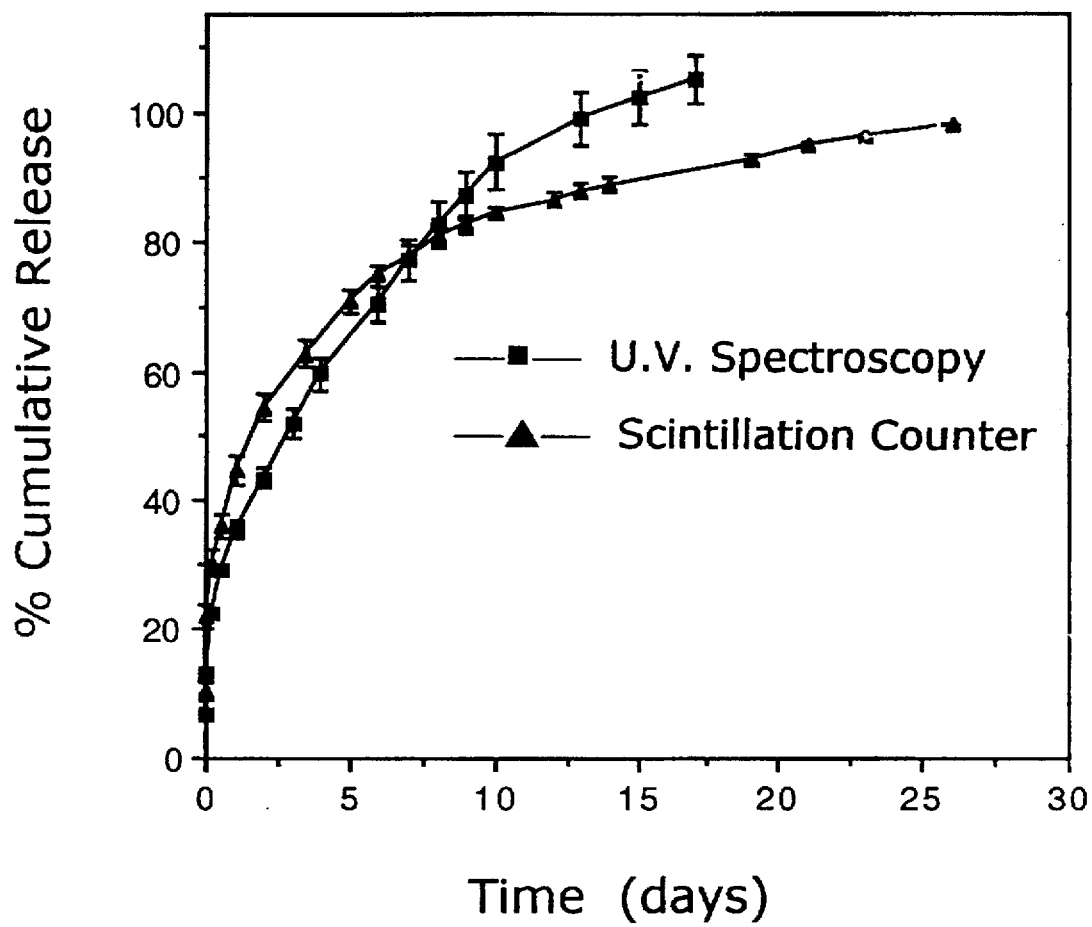
FIG. 1b is a graph of percent cumulative release versus time (days) for in vitro release from microspheres with contain either tritium labeled bupivacaine and unlabeled dexamethasone.

When microspheres loaded with unlabeled bupivacaine and radiolabled dexamethasone were prepared, the yield (weight of microspheres/weight of bupivacaine+weight of polymer) was 45%. The bupivacaine content was determined to be 75±1%. When microspheres loaded with unlabeled dexamethasone and radiolabeled bupivacaine were prepared, the yield was 50%, and the bupivacaine content was 73±2%. Comparison of the % cumulative release of both tritum labeled dexamethasone and tritium labeled bupivacaine, proves that dexamethasone was incorporated into the microspheres and that both substances were released at similar release rates. The comparison of the two techniques, U.V. spectroscopy and scintillation counting used to monitor the in vitro release of unlabeled and radiolabeled bupivacaine respectively, in FIG. 1b show that the same release rate occurred using the two techniques.

Rat Sciatic Nerve Blockade In Vivo

Figure 3A:
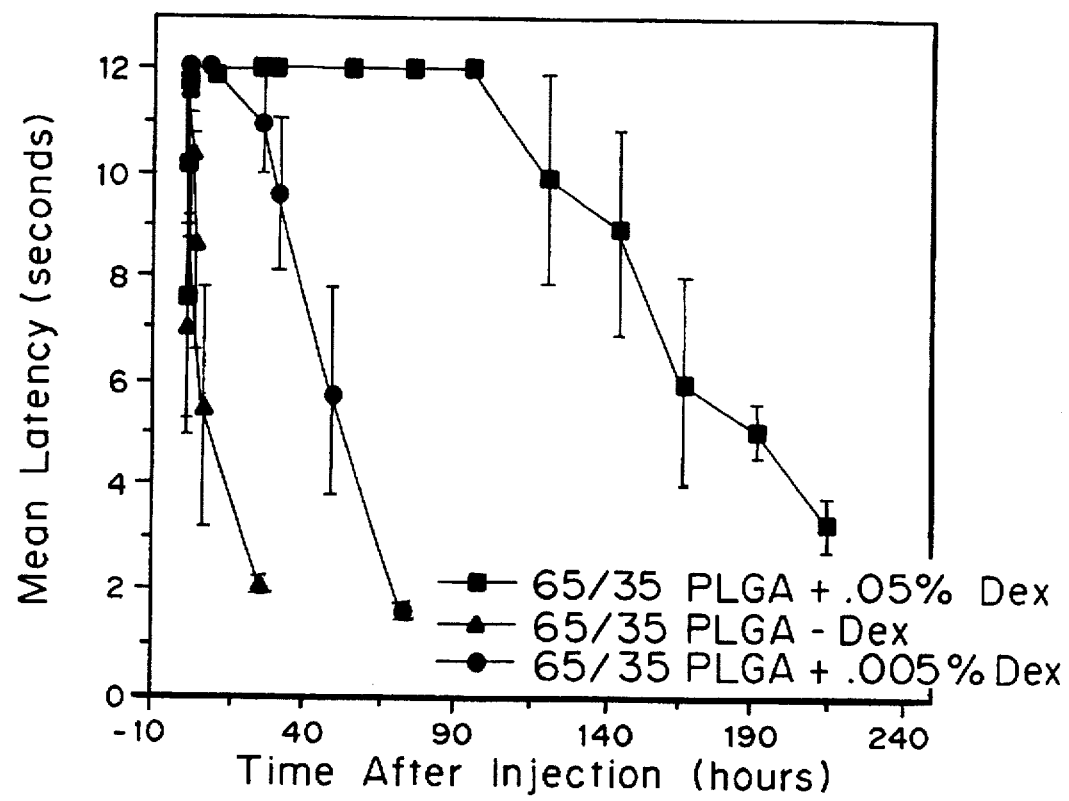
FIGS. 3a and 3b are graphs of the duration of latency versus time (hours), determined by sensory testing using the modified hot plate test (FIG. 3a) or by motor testing (FIG. 3b) for 75% bupivacaine loaded PLGA containing 0.05%, 0.005%, and 0% dexamethasone. Error bars indicate standard errors.
Figure 3B:
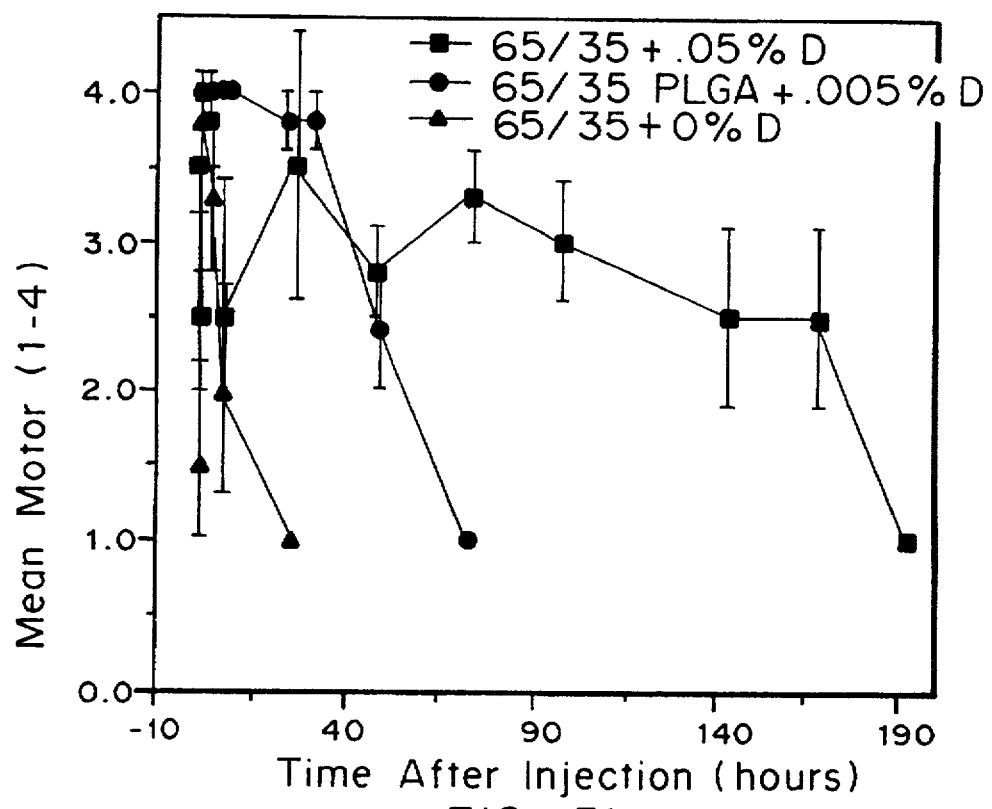
Figure 4A:
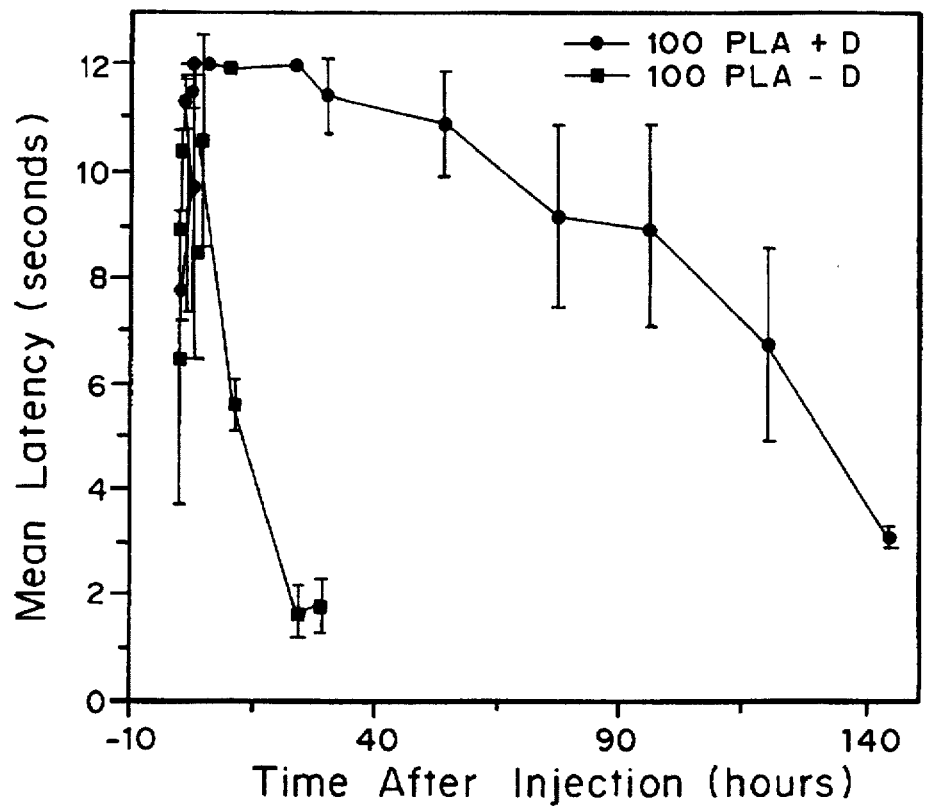
FIGS. 4a, b, c, and d, are graphs comparing the duration of latency versus time (hours), determined using the modified hot plate test for: 100 PLA microspheres loaded with 75% bupivacaine which contained 0.05% dexamethasone with corresponding microspheres which did not contain dexamethasone (FIG. 4a); PLGA 75:25 microspheres loaded with 75% bupivacaine which contained 0.05% dexamethasone with corresponding microspheres which did not contain dexamethasone (FIG. 4b); 65:35 PLGA microspheres loaded with 75% bupivacaine which contained 0.05% dexamethasone with corresponding microspheres which do not contain dexamethasone (FIG. 4c); and 50:50 PLGA microspheres loaded with 75% bupivacaine which contained 0.05% dexamethasone with corresponding microspheres which do not contain dexamethasone (FIG. 4d). Error bar indicate standard errors.
Figure 4B:
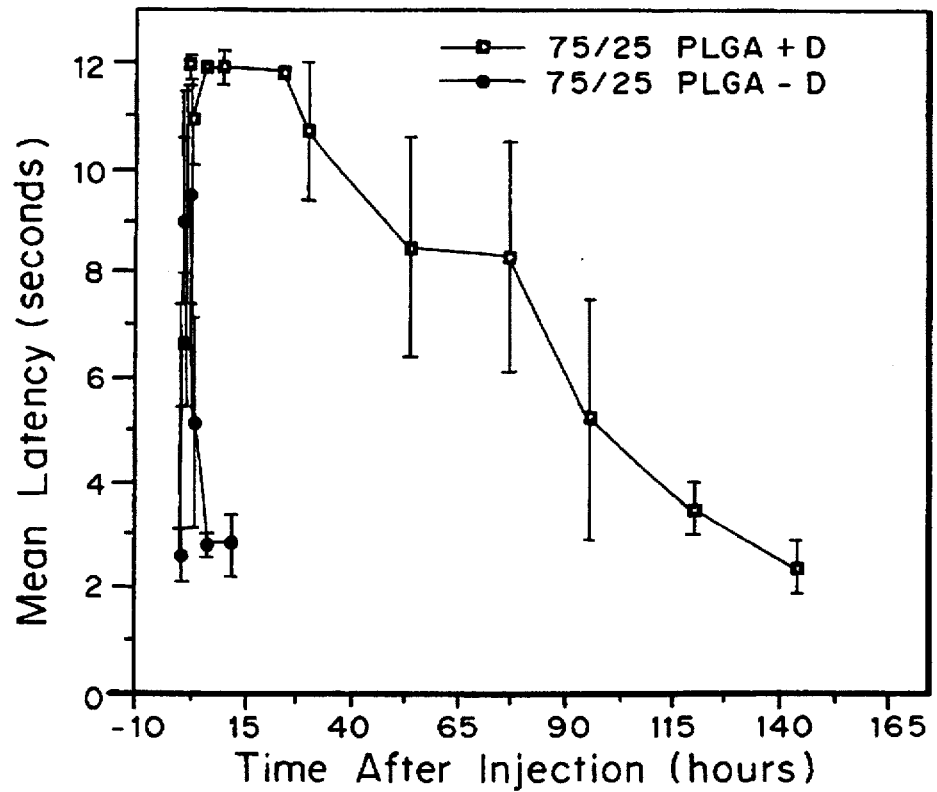
Figure 4C:
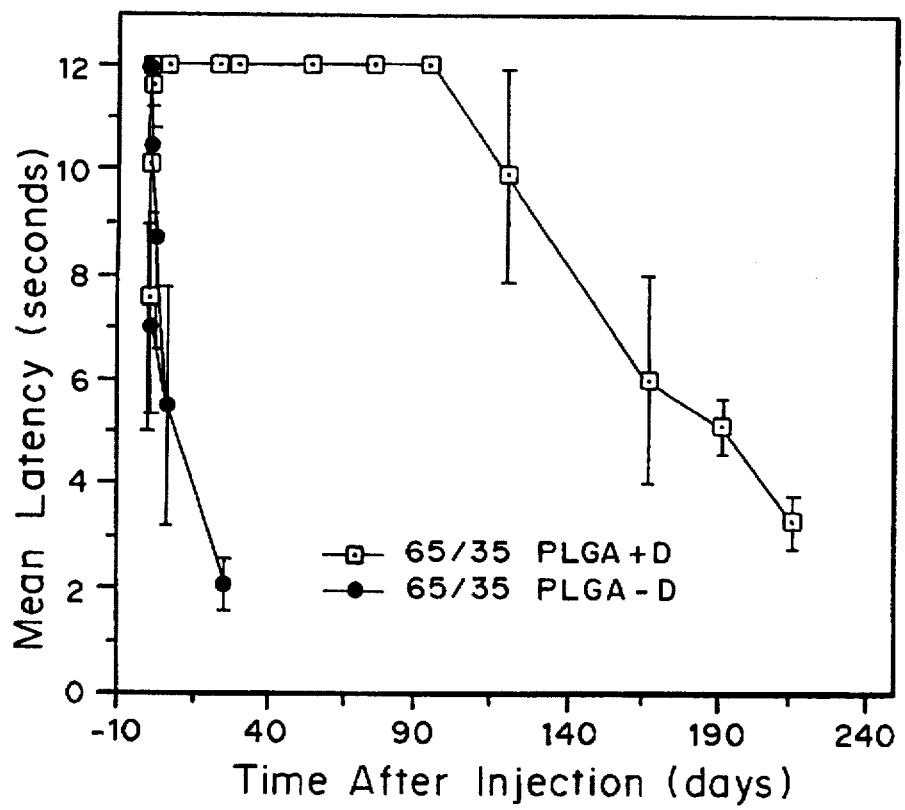
Figure 4D:
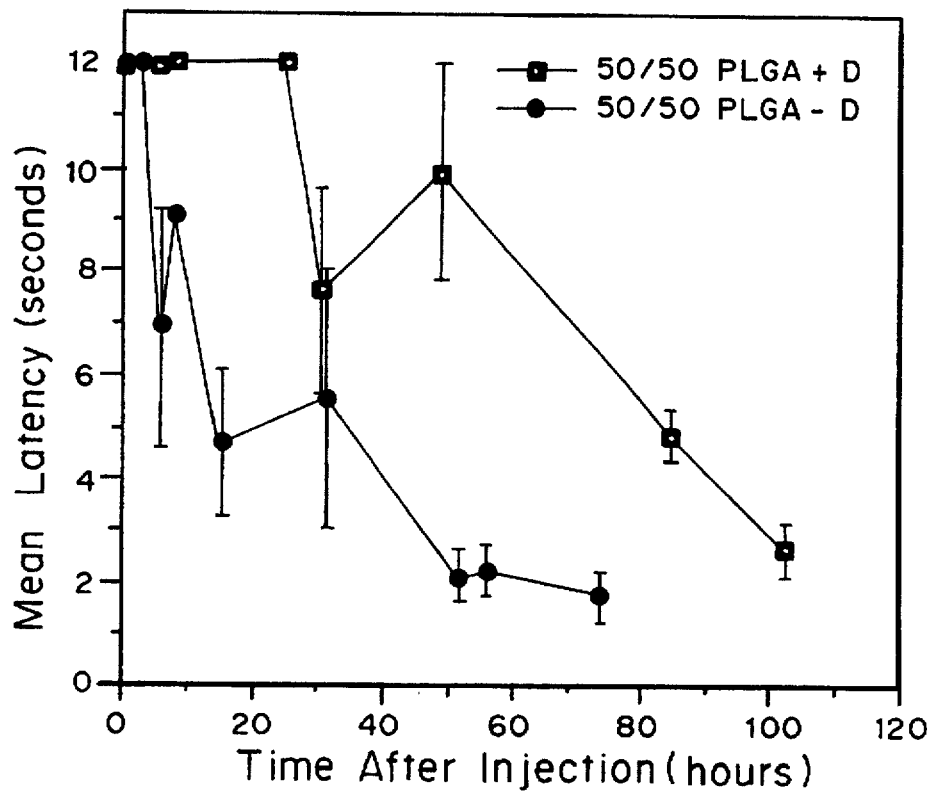

In order to determine the toxic response of the rats to various microsphere doses, the rats were injected with concentrations ranging from 50 to 450 mg of drug/kg of rat for each type of polymer. The corresponding plots of duration of block versus concentration of dexamethasone is shown in FIGS. 3a and 3b. No systemic toxicity, excessive sluggishness or death was observed even at the highest doses. FIGS. 4a–d compare the duration of sensory block for groups of rats injectd with bupivacaine loaded PLA 100, PLGA 75/25, PLGA 65/35 and PLGA 50/50 microspheres with and without incorporated dexamethasone. In each case, the presence of dexamethasone in the microspheres resulted in a 6–13 fold increase in the duration of block. Mean sciatic nerve block durations among treatment groups varied from 65±3 to 134±13 hours for microsphere formulations which contained dexamethasone. Control groups receiving injections of polymer microspheres containing no drug or dexamethasone or containing dexamethasone alone showed no sensory or motor block. A comparison of the latencies obtained from PLGA 65/35 microspheres which contained 0%, 0.005% and 0.05% dexamethasone at a dose of 150 mg/Kg of rat showed duration of the blocks were 8, 50 and 170 hours respectively as shown in FIG. 3a. The optimum dose and formulation was determined to be 150 mg of drug/kg of rat of PLGA 65/35 microspheres loaded with 75% bupivacaine and 0.05% dexamethasone, as this was the lowest dose which resulted in the longest duration of block.

The in vitro results showed that the bupivacaine was released from the microspheres in a controlled manner. In general, 24–40% of the bupivacaine was released in the first 24 hours, and approximately 7% released daily thereafter. After 5–8 days approximately 90% of the bupivacaine was released. The presence of dexamethasone in the microspheres did not significantly affect the in vitro release rates of bupivacaine and the in vitro results cannot account for the prolongation of block, due to the presence of dexamethasone observed in vivo.

The in vitro results obtained from the release studies on the radiolabeled microspheres proved that dexamethasone was incorporated into the microspheres and was released at approximately the same rate as bupivacaine (FIG. 1b). In FIG. 1b, the % cumulative release of bupivacaine versus time was overlaid for two different detection techniques, U.V. spectroscopy and scintillation counting. The two graphs paralleled each other, verifying the accuracy of the two detection methods.

The presence of 0.05% dexamethasone in microspheres significantly prolonged the duration of sciatic nerve block. That is, the block obtained using microspheres which contained 0.05% dexamethasone was up to 13 fold long than the block obtained using the corresponding microspheres which did not contain any dexamethasone. It was determined that 150 mg of microspheres/Kg of rat was the optimum dosage and any further prolongation of block obtained by using a higher dose of injecting a higher dose. The optimum dose and formulation was determined to be 150 mg of drug/Kg of rate of PLGA 65/35 microspheres which contained 75% bupivacaine and 0.05% dexamethasone (the mass median diameter was 70μ, determined using a coulter counter). Using this formulation a 134 hour sciatic nerve block was achieved.

EXAMPLE 3

Administration of Microspheres in Combination with Glucocorticoids in Solution Previous studies demonstrated that incorporation of 0.05% dexamethasone into either pellets or microspheres resulted in prolongation of block, from 70–100 hours when microspheres which contained 0.05% dexamethasone were used versus 50–60 hours in the case of microspheres which contained no dexamethasone. To further understand the mechanism, a model system was developed whereby different additives: steroids, steroidal anti-inflammatories, and non-steroidal antiinflammatories (NSAIDs), were placed in the injection fluid to determine if the block could be prolonged. In this model system, the additives were placed into the injection fluid immediately prior to injection, and the microspheres used contained bupivacaine, but no dexamethasone. If the additive was a solid, it was dissolved in ethanol and aliquots of concentrations which varied between 0.005 and 5% w/w added. If the additive was in liquid form, then the amount was added directly to the injection fluid.

Materials and Methods

Formulation of PLGA Microspheres and Protocol for In Vitro Release Studies

Formulation of Microspheres of 65:35 loaded with 75% bupivacaine with 0.05% dexamethasone 50 mg of PLGA 65:35 (High molecular weight, purchased from Medisorb) and 150 mg of bupivacaine free base (obtained from Perdue-Frederick) were dissolved in 0.1 ml of a solution of 5 mg of dexamethasone in 5 mls in $CH_2CL_2$ and 0.9 mls of $CH_2CL_1$. 1 ml of 0.3% polyvinyl alcohol (PVA) in 100 mM Tris buffer at pH 8.5, was added and the mixture vortexed 3 times for 15 seconds each time. The mixture was poured into 100 mls of 0.1% PVA in 100 mM Tris buffer. The microspheres were examined using the light microscope and the size distribution was determined to be between 10 and 110 microns. The $CH_2Cl_2$ was removed by heating the sample to 45° C. using a rotary evaporator at full vacuum for 15 minutes. The suspension of microsphere's in 0.1% PVA was filtered through 140, 60, and 20μ metal sleeves (Newark Wire Cloth Co.). Then the microspheres were frozen in liquid nitrogen and lyophilized overnight. Formulation of Microspheres which contained tritium labeled dexamethasone Radiolabeled dexamethasone was purchased form Amersham and an aliquot which contained 200,000 counts was added to cold dexamethasone and the microspheres were formulated as above.

Formulation of Microspheres which contained tritium labeled Bupivacaine

Radiolabeled bupivacaine was kindly donated by Dr. Gary Strichard from Brigham and Woman's Hospital. Again the bupivacaine was dissolved in ethanol and an aliquo which contained 200,000 counts was added to cold bupivacaine and the microspheres were formulated as above.

Analysis of the In Vitro Release of Either Tritium Labeled Dexamethasone or Bupivacaine The in vitro release studies were carried out as outlined above except that instead of monitoring the release by U.V. spectroscopy, the in vitro release was determined by adding 15 mls of Ecolume™ to each 2 ml aliquot of buffer, and the subsequent disintegrations were monitored using a scintillation counter.

Preparation of the Suspension

A ratio of 150 mg bupivacaine/kg was injected. The corresponding amount of microspheres is 200 mg/kg. The microspheres are weighed out and transferred to a 3 cc syringe via the plunger. The needle of the syringe is removed and the opening covered with parafilm. Carboxymethylcellulose sterilized by filtration through a 0.2 micron filter is used as the injection fluid.

The rats are tested at 0.5, 1, 2, 3, 6, 8 and 24 hours after injection and then once daily until the block wears off. The rat is motor and sensory tested each time as described above using a hotplate at 56° C.

RESULTS

The results are shown in Table 2.

TABLE 2

| PLGA Polymer 150 mg/kg + Additives | | | |
| --- | --- | --- | --- |
| # of rats | Additives (Conc) | Class of Additive | Duration of block (hrs. |
| 7 | Dexamethasone (0.05%) | Anti-Inflammatory/ Steroid (strong) | 50–60 |
| 5 | Dexamethasone (.005%) | Anti-Inflammatory/ Steriod (strong) | 5–6 |
| 5 | Dexamethasone (.5%) | Anti-Inflammatory/ Steriod (strong) | 24 *2 Rats Died 2 Weeks Later |
| 8 | Cholesterol (0.05%) | Steroid | 3–4 |
| 5 | Cholesterol (0.05%) | Steroid | 5 |
| 5 | Epinephrine (.05%) | Cardiovascular Drug | 6–7* Rats Became Sick |
| 5 | Ketorolac (0.5%) | Anti-Inflammatory (strong) | 6–7 |
| 5 | Ketorolac (5%) | Anti-Inflammatory (strong) | 6–7 |
| 5 | Methyl-predoisolone | Anti-Inflammatory/ | 20 |

TABLE 2-continued

PLGA Polymer 150 mg/kg + Additives

| # of rats | Additives (Conc) | Class of Additive | Duration of block (hrs.) |
|---|---|---|---|
|  | (5%) | Steroid (medium) |  |
| 7 | Methyl- predoisolone (0.5%) | Anti- Inflammatory/ Steriod (medium) | 25 |
| 5 | Estradiol (0.5%) | Steroids | 6–8 |
| 4 | Estradiol (0.05%) | Steroid | 7 |
| 71 | Hydrocortisone (0.5%) | Anti- Inflam/Steroid (weak) | 8–9 |
| 5 | Hydrocortisone (5%) | Anti- Inflam/Steriod (weak) | 13 |
| 5 | Testosterone (.05%) | Steroid | 10–15 |
| 5 | Betamethasone (.05%) | Anti- Inflam/Steroid (strong) | 40–45 |

Figure 5A:
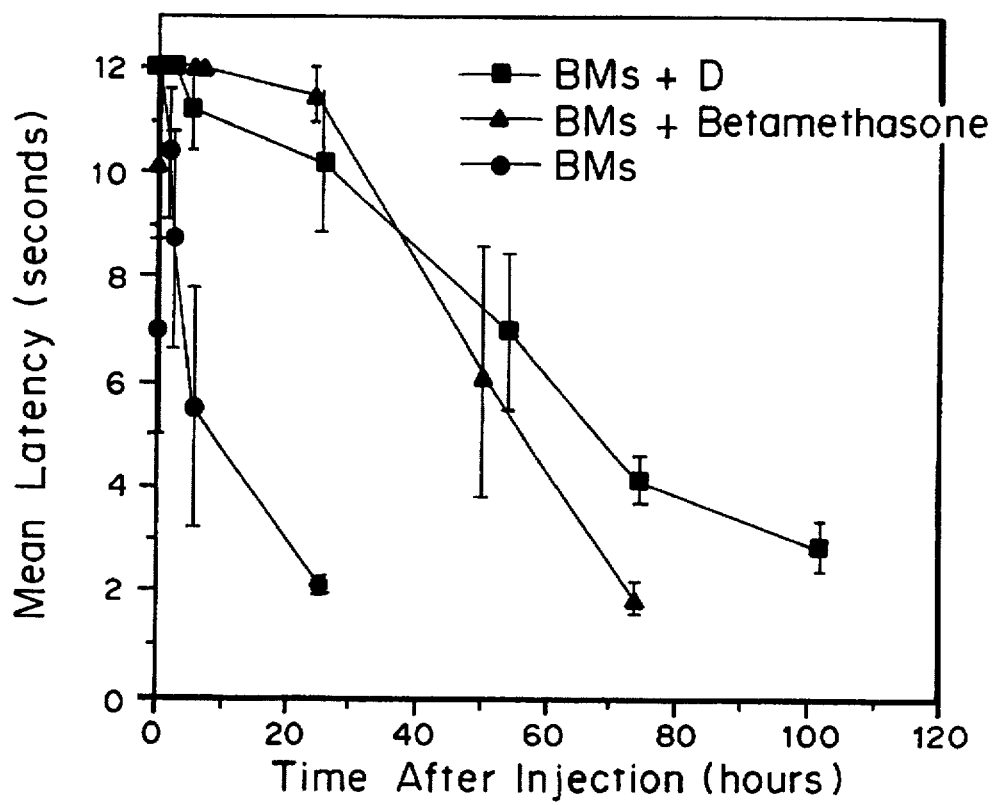
FIGS. 5a and b are graphs of the duration of sensory block (FIG. 5a) and of the duration of motor block (FIG. 5b) in hours after injection of bupivacaine loaded microspheres (circles), bupivacaine loaded microspheres with dexamethasone in the injection fluid (squares), and bupivacaine loaded microspheres with betamethasone in the injection fluid (triangles).
Figure 5B:
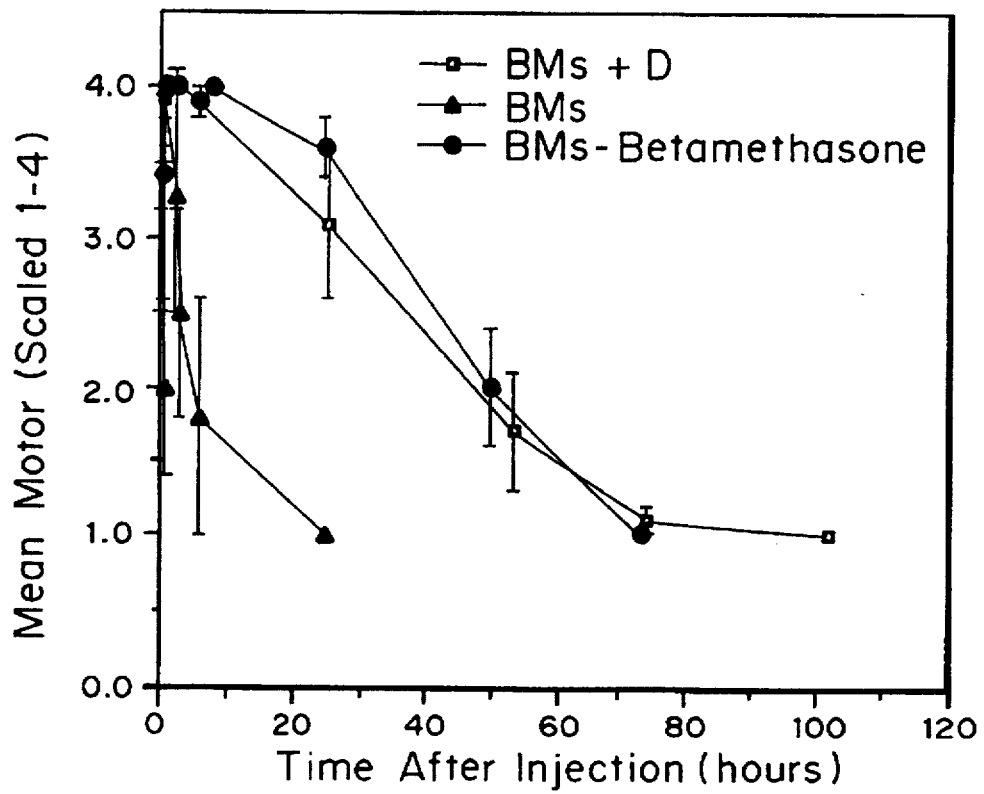

The results comparing sensory and motor block following administration of dexamethasone in the injection fluid with dexamethasone in the microspheres is shown in FIGS. 5a and 5b.

The results demonstrate that dexamethasone does not produce sciatic blockade by itself in solution, nor does it prolong blockade from bupivacaine in solution. Addition of dexamethasone in solution with bupivacaine in solution did not prolong blockade relative to bupivacaine in solution alone. The prolonged blockade previously observed seemed to require the presence of bupivacaine in microspheres.

A model system was developed in which dexamethasone was dissolved in ethanol and an aliquot of known concentration was added to the suspending medium which contained microspheres loaded with 75% bupiviaine. Addition of dexamethasone to the suspending medium in concentrations ranging from 0.05% to 0.5% prolonged the duration of blockade obtained using bupivacaine microspheres. Addition of 0.005% w/w bupivacaine did not result in a prolongation of the blockade obtained. The result of this model system was useful, because it permitted testing of a series of compounds over full concentration ranges for prolongation of sciatic block in vivo without the labor-intensive step of making a microsphere prep with each additive and each dose.

Studies were conducted to determine whether dexamethasone's prolongation of blockade is unique, or whether it can be replicated by: (1) other glucocorticoids, (2) other classes of steroids, or (3) other drugs with anti-inflammatory activity, including non-steroidals (NSAIDs). For example, it is well known that cholesterol and other steroids modify membrane lipid phase equilibria, and it is conceivable that effects on lipid physical state could perturb sodium channel function and amplify or prolong channel blockade from local anesthetics. The question was also raised as to whether the dexamethasone effect was due to changes in regional perfusion, analogous to epinephrine's effect.

Figure 6:
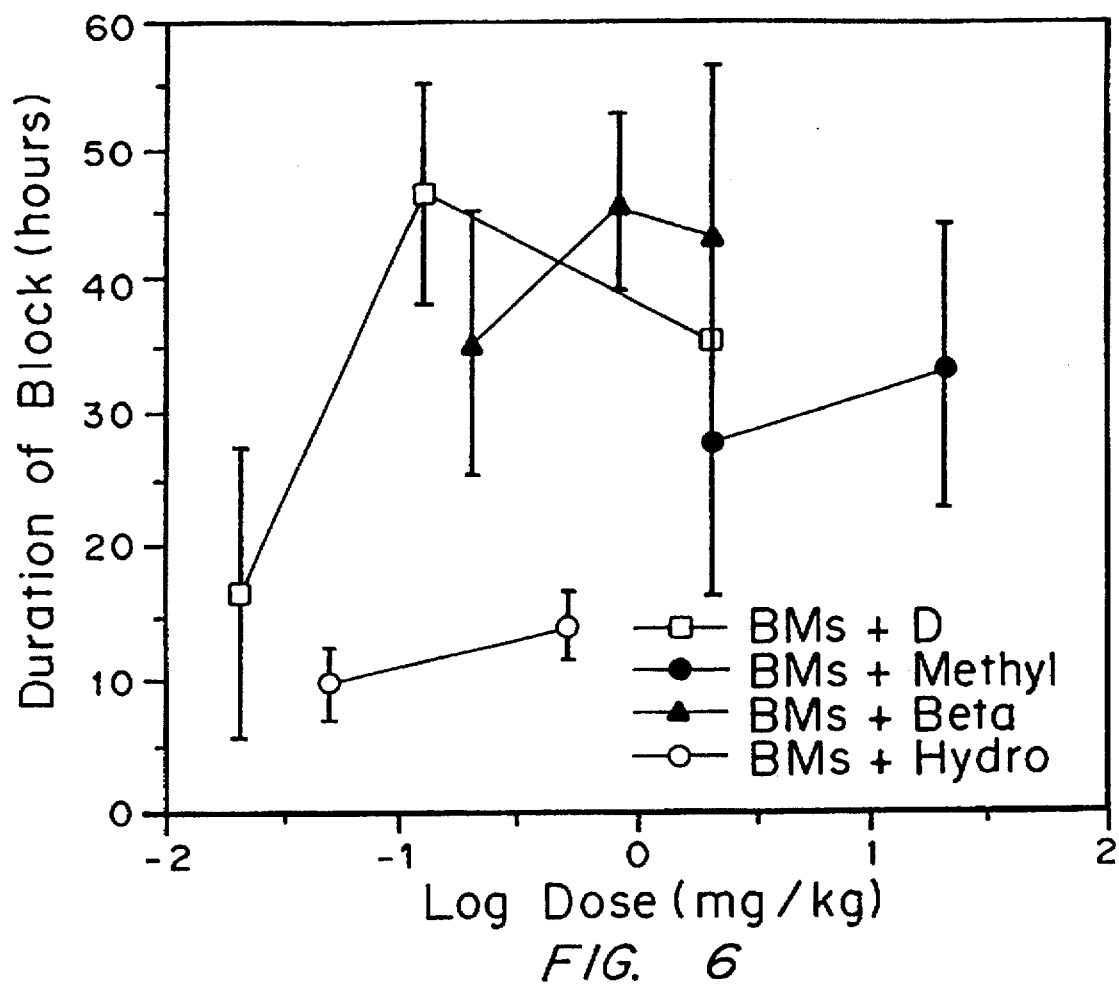
FIG. 6 is a graph of the duration of block (hrs) following administration of bupivacaine microspheres versus log of concentration (mg/kg) for various additives placed in the injection media: dexamethasone (square), methylprednisolone (closed circle), betamethasone (closed triangle), hydrocortisone (open circle).

Table 2 summaries the results of these experiments. FIG. 6 compares the effect of various glucocorticoids. It can be seen that:

1. High potency glucocorticoids such as betamethasone also produce prolongation of block up to 45 hours in duration.
2. intermediate potency glucocorticoids such as methyl-prednisolone produce intermediate degrees of block prolongation.
3. Weaker glucocorticoids such as hydrocortisone produce mild, but statistically significant prolongation of block.
4. The weaker prolongation of block by hydrocortisone cannot be made as effective as dexamethasone by further increasing its concentration in the suspending medium.
5. Estrogen have no block-prolonging effect. Testosterone may have shown mild prolongation of blockade; this effect warrants further repeating and controls.
6. NSAIDs and epinephrine did not substantially prolong blockade. Epinephrine in the doses used (0.05% in the suspending medium) produced considerable systemic toxicity, but no deaths.

Preliminary reports on the histologic effects are that they are benign, with no evidence of major axonal or demyelinating injury and only mild inflammation.

A long duration of block was produced using 150 mg/kg rat body weight with 75% bupivacaine loaded PLGA 65:35 microspheres. Doses as high as 600 mg/kg can be given with temporary somnolence as a side-effect, but no convulsions or cardiac arrests.

The dosing of dexamethasone in the microspheres (0.05%) is quite low, particularly considering its delayed release. Even when this concentration of dexamethasone was added in the suspending medium (permitting immediate access for absorption), no systemic effects were found. In one experiment using dexamethasone 0.5% in the suspending medium, no immediate toxicities occurred, but among five rats there were two deaths at 12–15 days post injection, and at the same time a third rat appeared thin and pale.

Experiments confirmed that 65:35 PLGA polymers were preferable to, either 75:25 PLGA or 100% PLA, both in terms of (1) the reliability, intensity and duration of sciatic nerve block, (2) each of dispersal and injectability. A blockade of 30–40 hours was observed with PLGA 50:50 over the PLGA 65:35 microspheres, indicating no advantage.

Modifications and variations of the present invention, a biodegradable controlled release device for the prolonged and constant delivery of a local anesthetic agent, will be apparent to those skilled in the art from the foregoing detailed description of the invention. Such modifications and variations are intended to come within the scope of the appended claims.

We claim:

1. A method for providing sustained local numbness or pain relief at a site in a patient comprising
administering at a site in a patient a local anesthetic incorporated into a device consisting essentially of a biocompatible, biodegradable polymer, wherein the local anesthetic is present in a concentration effective to achieve local numbness or pain relief at the site, and an amount of a glucocorticoid effective to prolong the local numbness or pain relief at the site.

2. The method of claim 1 wherein the polymer is selected from the group consisting of polyanhydrides, copolymers of lactic acid and glycolic acid, polyorthoesters, proteins, and polysaccharides degrading at least fifty percent in less than six months following implantation into the patient.

3. The method of claim 1 wherein the device is in a form selected from the group consisting of microparticles, microspheres, and microcapsules.

4. The method of claim 1 wherein the anesthetic is selected from the group consisting of bupivacaine, dibucaine, etidocaine, tetracaine, lidocaine, xylocaine and salts thereof.

5. The method of claim 1 wherein the anesthetic is incorporated into the polymer at a percent loading of between 0.1% and 90% by weight.

6. The method of claim 5 wherein the glucocorticoid is incorporated into the polymer at a percent loading of between 0.01 and 30% by weight.

7. The method of claim 1 wherein the glucocorticoid is administered in a solution with the device.

8. The method of claim 2 wherein the device is a microsphere having a diameter of between 10 and 200 microns.

9. The method of claim 1 wherein the polymer does not elicit inflammation following implantation into a patient.

10. The method of claim 1 further comprising administering the device by injection.

11. A device for sustained local numbness or pain relief at a site in a patient comprising a local anesthetic incorporated into a device consisting essentially of a biocompatible, biodegradable polymer, wherein the local anesthetic is present in a concentration effective to achieve local numbness or pain relief at a site in a patient, and an amount of a glucocorticoid effective to prolong the local numbness or pain relief at the site.

12. The device of claim 11 wherein the polymer is selected from the group consisting of polyanhydrides, copolymers of lactic acid and glycolic acid, polyorthoesters, proteins, and polysaccharides degrading at least fifty percent in less than six months following implantation into the patient.

13. The device of claim 11 wherein the device is in a form selected from the group consisting of microparticles, microspheres, and microcapsules.

14. The device of claim 11 wherein the anesthetic is selected from the group consisting of bupivacaine, dibucaine, etidocaine, tetracaine, lidocaine, xylocaine and salts thereof.

15. The device of claim 11 wherein the anesthetic is incorporated into the polymer at a percent loading of between 0.1% and 90%.

16. The device of claim 15 wherein the glucocorticoid is incorporated into the polymer at a percent loading of between 0.01 and 30% by weight.

17. The device of claim 12 wherein the device is a microsphere having a diameter between 10 and 200 microns.

18. The device of claim 11 wherein the glucocorticoid is in a solution with the microspheres.

19. The device of claim 11 wherein the polymer does not elicit inflammation following implantation into a patient.

20. The device of claim 11 further comprising a pharmaceutically acceptable carrier for administering the device by injection.

21. The device of claim 11 wherein the polymer incorporating the local anesthetic is coated with a material preventing inflammation as a result of implantation of the polymer.

* * * * *